United States Patent [19]

Ciaccio et al.

[11] 4,073,692

[45] Feb. 14, 1978

[54] METHOD AND APPARATUS FOR AUTOMATED MEASUREMENT OF ENERGY OXYGEN

[76] Inventors: Leonard L. Ciaccio, 55 Yardley Court, Glen Rock, N.J. 07452; Klaus Hameyer, 947 Round Bay Road, Norfolk, Va. 23502

[21] Appl. No.: 570,089

[22] Filed: Apr. 21, 1975

[51] Int. Cl.$^2$ ............................................. C12B 1/00
[52] U.S. Cl. ............................ 195/103.5 R; 195/142; 195/143
[58] Field of Search ................. 195/1.7, 1.8, 103.5 R, 195/109, 142–144; 204/1 P, 1 V; 23/230 B, 253; 210/2, 4, 7, 15, 17, 20; 128/2.07, 2.08

[56] References Cited

U.S. PATENT DOCUMENTS

| 3,510,406 | 5/1970 | Stack, Jr. ............................ 204/1 P |
| 3,723,255 | 3/1973 | Walden et al. ....................... 195/109 |

FOREIGN PATENT DOCUMENTS 1,263,754   1972   United Kingdom.

Primary Examiner—R. B. Penland

[57] ABSTRACT

There is described herein a method and apparatus for determining the total consumption of dissolved oxygen in a liquid by organic materials contained therein in the presence of a biological growth culture. The invention includes providing a supply of liquid, preferably water, which is saturated with air. A liquid sample containing the organic material is supplied to the air saturated liquid. The combined mixture is then supplied, at a fixed volumetric rate, to a tube of predetermined length which contains the biological "culture". The biological growth, utilizing the oxygen dissolved in the liquid mixture, reacts with the organic material contained therein resulting in certain synthesized materials and other oxidation products. At the exit end of the tube oxygen detecting means is positioned which measures the oxygen contained in the liquid mixture after exposure to the biological growth. This measurement when plotted against time gives an indication of the total amount of oxygen consumed due to the assimilation of the organic material by the biological growth culture.

Alternately, the readout of the oxygen detecting means can be supplied directly to an integrating amplifier or similar device, to which a set of system parameters can be supplied as constants. The output of such a device will represent the oxygen consumed.

18 Claims, 6 Drawing Figures

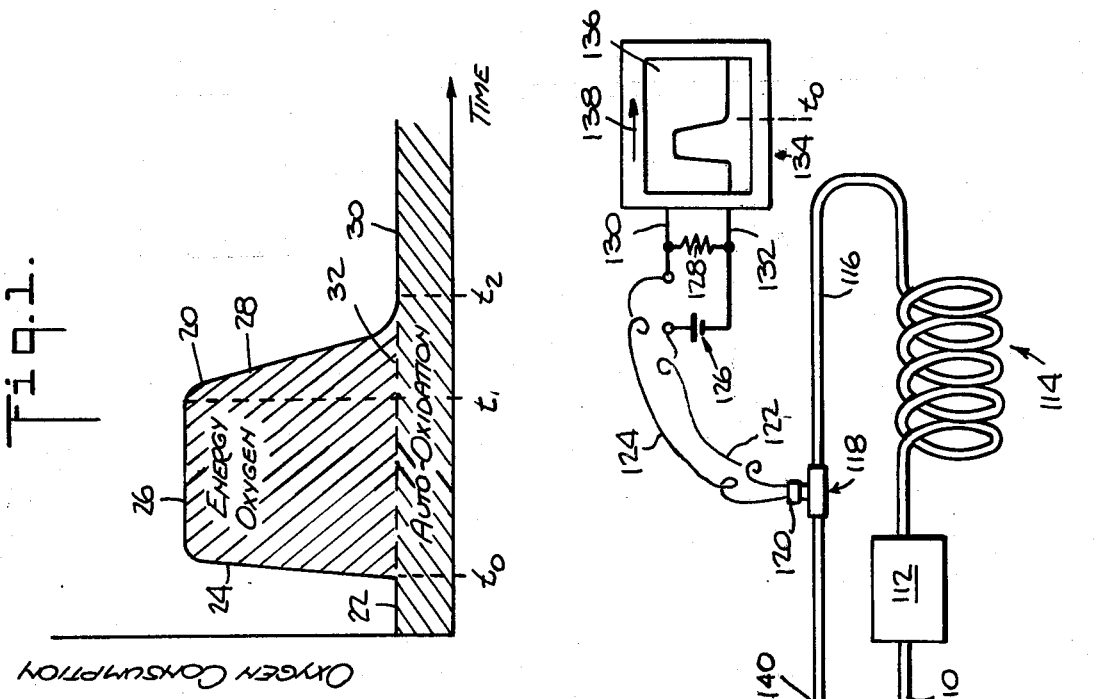
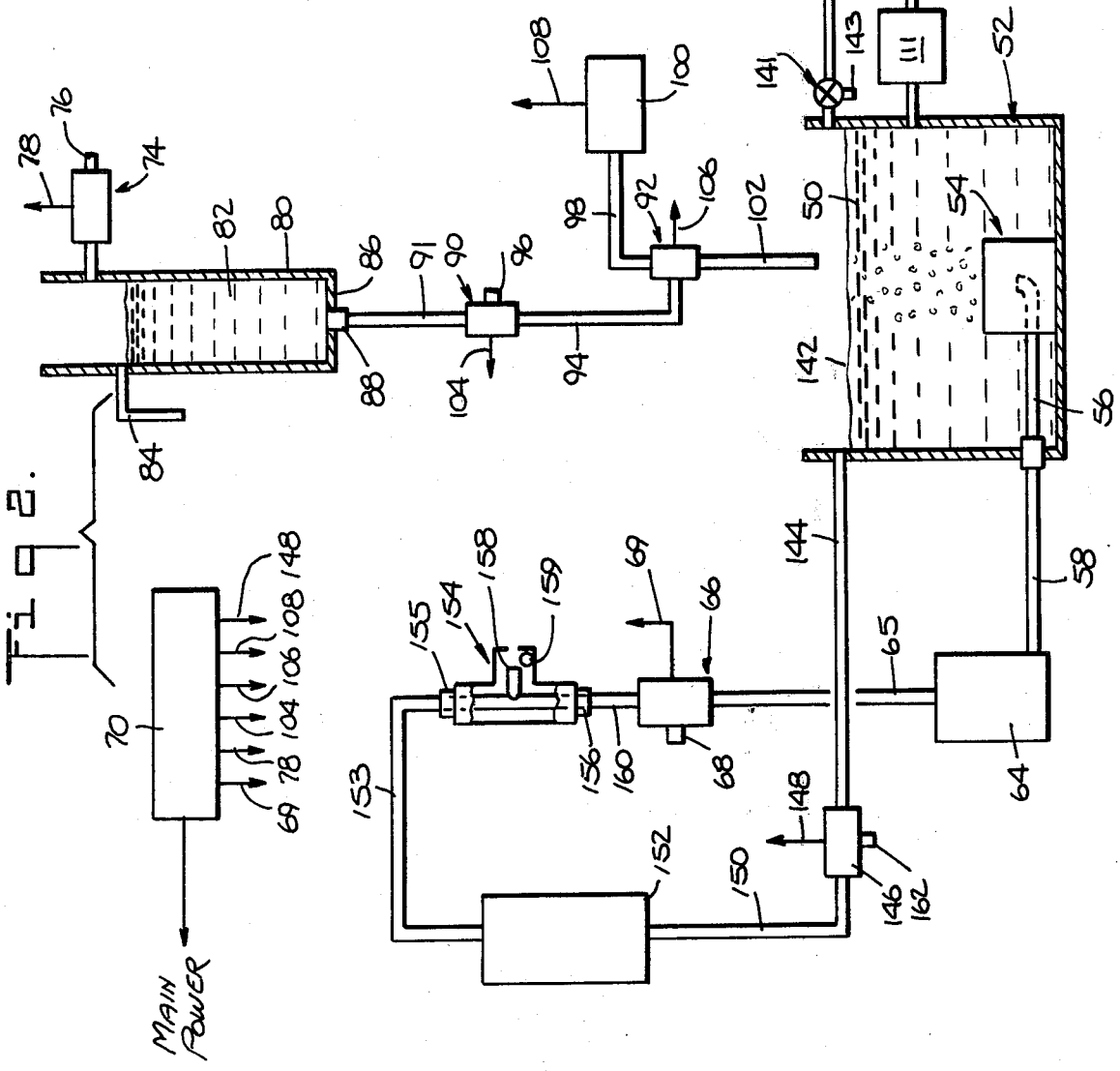

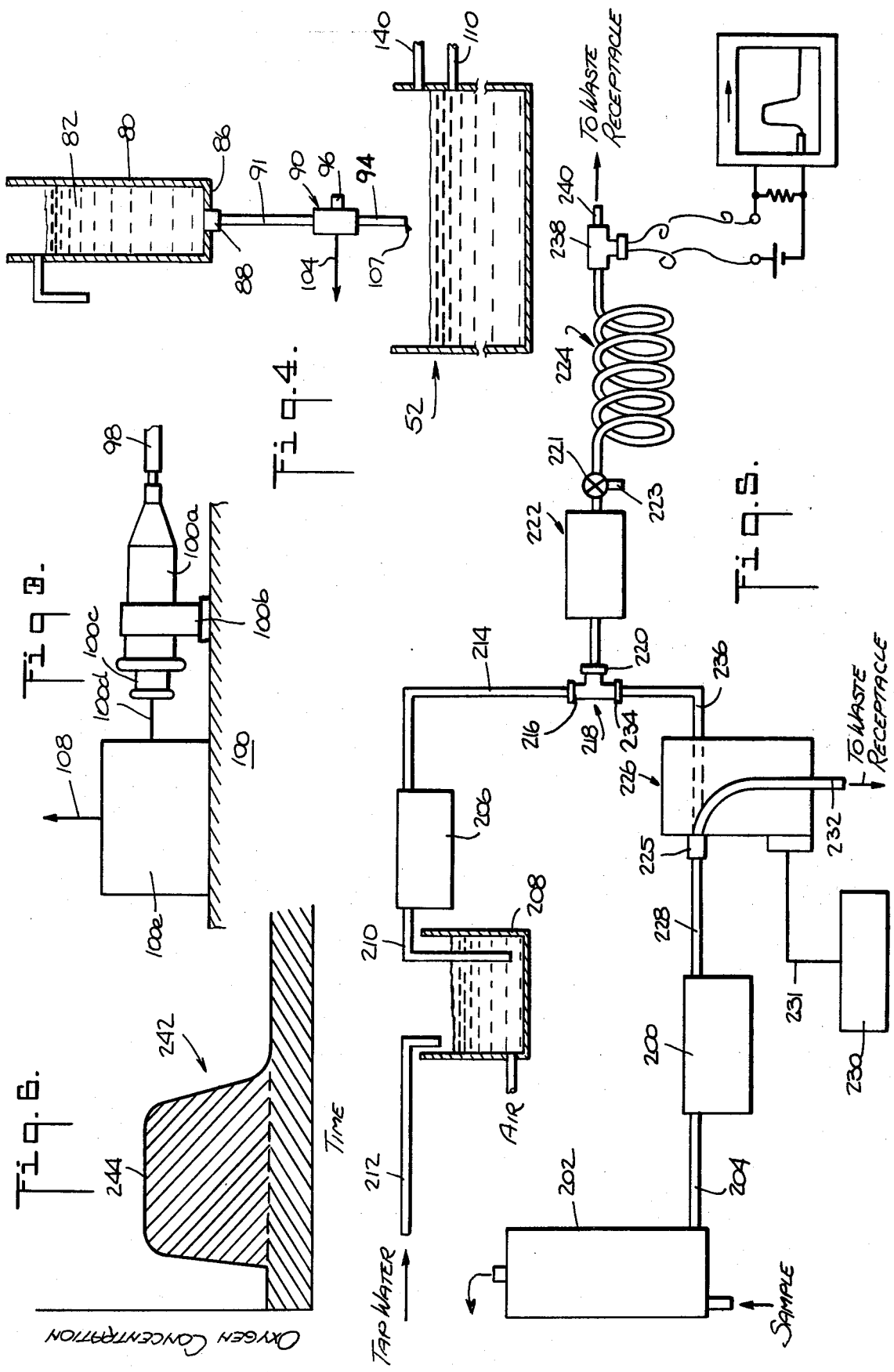

METHOD AND APPARATUS FOR AUTOMATED MEASUREMENT OF ENERGY OXYGEN

BACKGROUND OF THE INVENTION

1. Field of the Invention

This invention relates to the measurement of oxygen consumption and particularly to the measurement of the comsumption of oxygen in a biological oxidation system.

2. Description of the Problem and the Prior Art

Oxygen is consumed in a biological oxidation system, (e.g. an aerobic culture of microorganisms) by the action of the microorganisms while organic material is oxidized into synthesized cell material and other oxidation products and while synthesized cell material is oxidized further. The amount of oxygen consumed by such a system is of importance in sanitary engineering applications which are concerned, for example, with waste streams (both before and after treatment), effluents from treatment processes, and the quality of natural waters. It is common to express the comsumption of oxygen in a biological oxidation system in terms of the biochemical oxygen demand (BOD), which is the amount of oxygen consumed by the system in a predetermined interval, typically a period of five days. The measurement, however, may require a period as long as twenty days to determine the ultimate amount of oxygen consumed by the system.

It is important to be able to make a fundamental measurement of oxidiation in a biological oxidation system in a much shorter period of time, such as a fraction of an hour. For example, in the treatment of sewage, it is desirable to be able to continuously monitor the oxidation processes in order to determine the degree of completion and progress of oxidation reactions.

It has been found that a fundamental quantity to be measured in any biological oxidation system is the amount of oxygen required to convert organic material in the system to new cell material and other oxidation products. This amount of oxygen, herein, designated energy oxygen is distinct from the oxygen consumed by the system in auto-oxidation, which is the term given to oxidation of previously synthesized cell material. It is generally believed in the literature that the energy oxygen per unit quantity of a particular organic material is constant regardless of the nature of the biological oxidation process. Hence, for a particular material, energy oxygen is the same whether the material is being oxidized slowly or rapidly. Thus a technique for measuring energy oxygen, wherein oxidation is accelerated, provides a basis for making a fundamental measurement of the oxidation process in a relatively short time.

In the past, the measurement of oxygen consumption had generally been limited to the laboratory where direct measurements were made using respiration devices. A disadvantage of such respiration devices is that they provide oxygen consumption data only for a small captive sample contained within the respirometer. Measurements cannot be made of the rate of oxygen consumption in systems outside the respirometer, and hence the respirometers are not suitable for the continuous monitoring of oxidation processes.

In response to the problems mentioned above, Vernon T. Stack, Jr. developed a biological oxygen demand analyzer which is described in detail in U.S. Pat. Nos. 3,510,406 and 3,510,407. The U.S. Pat. 3,510,406 describes an apparatus which includes a pair of dissolved oxygen probes. The system includes what could be called a sludge pot wherein the bacterial growth, sludge, and the liquid sample are mixed. The mixed solution of sludge and sample are then passed through a sealed fluid path, with the dissolved oxygen probes positioned at the inlet and outlet openings of the path. The organic material in the sample combines with the oxygen and bacterial growth in the sludge pot, all of which are passed through the sealed path. The oxygen concentration in the liquid before and after passage through the fluid path is determined by the corresponding dissolved oxygen probes positioned at the inlet and outlet. The reading from the inlet probe is delayed for a time equal to the transit time. The probe readings are then fed to a time integrating device, such as a recorder. The signal indicating the difference between the two DO probe readings gives an indication of the rate of oxygen comsumption.

This system suffers from numerous disadvantages. First of all, since the bacterial growth combines with the sample in the sludge pot, oxygen comsumption occurs not only while the combined liquid mixture passes through the sealed fluid path but also in the sludge pot itself. Thus the oxygen rate as determined from the time recorder chart is not totally accurate. A correction factor has to be introduced to compensate for the additional oxygen consumed in the slude pot itself. Moreover, due to the fact that a pair of oxygen probes are employed and a differential reading between these has to be taken, the difficult task of matching and calibrating the two probes influences the accuracy of the oxygen comsumption rate determination. Further, the storage of the inlet probe reading for the period of time it takes the sample to pass through the sealed path necessitates a certain electronic time delay capacity which makes the equipment additionally complex. Also, in a continuously monitoring system which necessitates the sequential analysis fo liquid samples to detect changing levels of organic material, the time between samples is an important factor. The time between samples is excessively long due to the fact that the decant portion of the cycle, i.e., the liquid bleed-off portion, is delayed excessively while the sludge in the sludge pot settles out to a level below the decant level. Finally, the pumping of the sludge through the system tends to foul up the oxygen probes and the pumping equipment which necessitates mechanical stirrers and brushing apparatus to remove whatever sludge might accumulate on the system hardware.

It is therefore an object of this invention to improve the accuracy of a biological oxidation analyzer system.

It is another object of this invention to increase the number of sample evaluations per unit time in a biological oxidation analyzing system.

It is still another object of this invention to provide a biological oxidation system which will be free of the problems associated with maintaining large amounts of sludge, thereby extending its life and usefulness.

It is yet another object of this invention to make a relatively fast measurement of the oxygen consumption.

It is another object of this invention to determine the energy amount of oxygen consumed by a biological oxidation system.

It is still another object of this invention to provide a relatively less complex and more reliable biological oxidation system.

SUMMARY OF THE INVENTION

The invention determines the total consumption of dissolved oxygen by a suitable biological growth while assimilating organic material. It includes means of containing and saturating a liquid, preferably water, with air as a source of oxygen. Means are provided for adding a liquid containing organic material to the liquid containing the dissolved oxygen. The resulting mixture is then moved at a fixed volumetric rate to a vessel containing a biological growth. The biological growth, in the presence of the dissolved oxygen, reacts with the organic material converting the latter into synthesized cell material as well as other oxidation products. Means are provided at the exit orifice of the vessel containing a biological growth medium for measuring the amount of oxygen remaining in the mixture of sample and previously air saturated liquid. This measurement when plotted against time gives an indication of the total amount of oxygen consumed by biological organisms in the presence of the organic material.

Alternately, the read out of the oxygen detecting means can be supplied directly to an integrating amplifier or similar device. For a set of system parameters fed in as constants to the integrator, the output of the latter itself represents the oxygen consumed, energy oxygen.

Means for aerating and agitating the mixture are provided to create a supply of air saturated liquid. Additionally, pumping means are provided which, after a particular sample is evaluated and the liquid is returned to the mixing vessle, removes an amount of liquid equivalent to that which contained the organic material. This allows for introduction of a fresh sample of liquid containing organic material and a repetition of the process. The frequency with which these successive operations can be made enable a nearly continuous determination of the rate of consumption of dissolved oxygen. The means of supplying liquid containing organic material may include a means for intermediate storage utilizing the principles of hydrostatic pressure to supply a predetermined amount of sample liquid on successive occasions.

An alternate embodiment eliminates a return of the monitored liquid mixture to the mixing vessel. The pumping rates are adjusted to insure the proper concentration of organic material, typically a polutant and dissolved oxygen in the liquid mixture. After the mixture passes through the biological growth medium, it is deposited directly in a waste receptacle or drain.

A variation on the last mentioned embodiment makes it suitable for continuously monitoring instantaneous changes in the oxygen consuption and thus the variation in pollutant level. A recorder is first calibrated for a maximum energy oxygen consumption condition for a known pollutant concentration. Subsequent recorder variations provide a measure of the deviation of pollutant concentration from the known level.

BRIEF DESCRIPTION OF THE DRAWINGS

Reference is now made to the accompanying drawings for a better understanding of the nature and objective of the invention. The drawings illustrate the best embodiment presently contemplated for carrying out the objectives of the invention, and are not to be construed as restrictions or limitations on its scope. In the drawngs:

FIG. 1 is a characteristic curve showing the rate of oxygen consumption versus time for a typical aerobic biological oxidation system.

FIG. 2 is a schematic representation of the invention.

FIG. 3 is one embodiment of a portion of the invention shown in schematic representation.

FIG. 4 is another embodiment of that portion of the invention shown in FIG. 3.

FIG. 5 is another embodiment, in schematic form of an overall arrangement which employs the principles of the invention.

FIG. 6 is a graph useful in understanding the operation of the embodiment of FIG. 5.

DESCRIPTION OF THE PREFERRED EMBODIMENT

In order to have an understanding of the reactions between organic material and suitable biological growths a brief discussion thereof will be presented before proceeding with a detailed description of the present invention.

Referring to FIG. 1, a curve 20 is shown graphically representing the rate of oxygen consumption, also referred to as the uptake rate, versus time for a typical aerobic biological oxidation system. The curve represents the oxygen uptake rate per unit quantity of material in the system, and hence is normalized. Curve segment 22 represents the rate of auto-oxidation i.e., the uptake rate when no organic material other than cellular material is present in the system. The following equation represents the reactions that takes place during auto-oxidation.

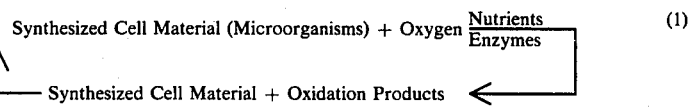

(1) Synthesized Cell Material (Microorganisms) + Oxygen $\xrightarrow{\text{Nutrients/Enzymes}}$ Synthesized Cell Material + Oxidation Products It will be noted that synthesized cell material in the presence of microorganisms and oxygen, as well as nutrients and enzymes, leads to the production of further synthesized cell material plus oxidation products. The reaction represented by Equation 1 is a closed cycle reaction, and theoretically continues in a closed system until there are no longer any viable microorganisms present.

At time $t_o$ organic material is introduced into the system. Soon after the introduction of the organic material, accelerated consumption of oxygen takes place, as represnted by the almost vertical curve segment 24 which levels off into curve segment 26. At time $t_1$ the oxygen uptake rate commences to decrease, as represented by curve segment 28, until time $t_2$ when the curve levels off into segment 30.

Between the times $t_o$ and $t_2$, not only is auto-oxidation taking place, as represented by equation 1, but other oxidation reactions are also occurring as represented by the following equation:

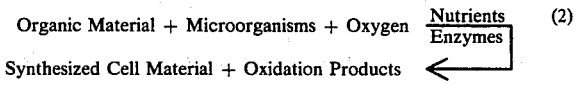

(2) Organic Material + Microorganisms + Oxygen $\xrightarrow{\text{Nutrients/Enzymes}}$ Synthesized Cell Material + Oxidation Products Equation 2 represents the synthesis of organic material into cell material and other oxidation products. At time $t_2$ in FIG. 1, the synthesis or organic material is complete, and hence none of the organic material originally fed remains, so that only auto-oxidation, represented by Equation 1, and segment 30 takes place. At time $t_2$ the system is said to be stabilized.

The period between times $t_o$ and $t_2$ may be relatively short in the event that the concentration of microorganisms is sufficiently high in the stabilized culture to which the sample of organic material is added. With a proper ratio of microorganisms to organic material, this time period can be as short as a quarter of an hour. It should be noted that in any system as represented in FIG. 1, a sufficient supply of oxygen should be maintained at all times to satisfy the needs of auto-oxidation as well as synthesis.

Referring to FIG. 2, there is depicted in schematic form a preferred embodiment of the invention as presently contemplated. It includes a supply of air saturated water 50 stored in an aeration cell 52. Positioned at the bottom of the cell is an aeration stone, 54. This, typically, is a porous, ceramic or even a suitable plastic material.

The interior of the stone is connected, via tubing 56 through the sidewall of the aeration cell 52 and tubing 58 to a supply of oxygen - typically this is the surrounding air. The tubing 58 is connected to the air outlet of a diaphragm air/vacuum pump 64 similar to Neptune Dynapump Model #3, manufactured by Neptune Products, Inc., Dover, N. J.

When air is forced through the connecting tubing, 56 and 58, into the interior of the stone, it is dispersed from the latter into water 50 in very fine bubbles, with the result that the water becomes quickly saturated with air. The stone can have any shape – cylindrical, spherical, etc. Alternately the stone can be replaced by a fritted disc positioned in a plane parallel to the bottom of the cell 52 and contiguous with the sidewalls. In this arrangement air would be supplied beneath the disc with it then being dispersed into the water above through the fine holes in the disc.

Whatever the form, the purpose of these is to facilitate the dispersion of small bubbles of air into the liquid in order to quickly saturate the latter, and to agitate and mix the sample with the air saturated water.

The vacuum outlet of the Neptune pump in turn, is connected via tubing 65 to a solenoid valve 66 similar to Model #V514380 manufactured by Skinner Precision Industries, Inc., New Britain, Conn., and then to the "outside" air via valve intake port 68. The operation of the solenoid valve is controlled via control line 69 by Micro Switch Timer, 70. The latter, preferably, has a one hour cycle. A suitable timer for this application would be Model #MC8 manufactured by Industrial Timer Corp., Parsippany, N. J.

The sequence of operation controlled by timer 70 will be discussed hereinafter.

Control line 69 is shown as an arrow emanating from valve 66 and timer 70. It is to be understood that this schematically represents an electrical connection suitable for conveying adequate electric power to the valve from the time and that it is shown as depicted for reasons of clarity only. Electrical connections between the timer and other valves and pumps in the system are similarly shown.

The next aspect of the invention is the sampling system whereby a predetermined amount of sewage or process effluent sample is periodically and reproduceably supplied to the aeration cell 52. An external pump 74 such as Little Giant Submersible Pump, Model #2-SMD, manufactured by Little Giant Pump Co., Oklahoma City, Oklahoma connected to the sample source through intake duct 76 is powered through control line 78 by the timer 70. At an appropriate point in the operational cycle of the system, the external pump 74 pumps a sample into the sample cylinder 80. The level of the sewage or process effluent sample 82 in the cylinder 80 is controlled by an overflow tube 84 which bypasses excessive amounts of the sample liquid into a waste receptacle or drain not shown. At the bottom 86 of the cylinder 80 is an exit port 88 which is connected to a three-port solenoid valve 90 via plastic tubing 91. One port of solenoid valve 90 is connected to another three-port solenoid valve 92 via tubing 94 with the remaining port 96 connected to the waste receptacle. The solenoid valve 92 has one outlet port connected via tubing 98 to a "syringe pump" 100, and the second port feeding the aeration cell 52 via tubing 102. The sequential operation of solenoid valves 90 and 92 is controlled by timer 70 via control lines 104 and 106 respectively. Again this sequence will be discussed hereinafter. Solenoid valves 90 and 92, could be a type identical to solenoid vlave 66.

As just noted one outlet port of solenoid valve 92 is connected to a "syringe pump". Referring to FIG. 3, the so-called "syringe pump" 100 is shown to include a standard syringe, 100a, which for purposes of this invention might be a 50cc plastic type syringe manufactured by the Becton-Dickinson Company of Rutherford, N.J. The syringe is held in a fixed position by mount 100b. The plunger 100c of the syringe is connected via connecting rod 100d to a suitable pump 100e which responds to a control voltage supplied by timer 70 over control line 108. A suitable pump, 100e, would be model #351 Syringe Pump, manufactured by Sage Instruments Div., Orion Research, Inc., Cambridge, Mass. when energized, the pump 100e acting through connecting rod 100d draws the plunger out of the syringe 100a thereby filling the latter with a portion of the sample to be evaluated - supplied via tubing 98 (at this time valves 90 and 92 would be conditioned to allow passage of the sample into the syringe). At the appropriate point in the system cycle as controlled by the system timer 70, the pump 100e reverses itself causing the plunger 100c to return to its initial position within the syringe whereby the sample contained therein, is forced out. (Valve 92 at this point would be conditioned to enable the fluid in the syringe to pass therethrough and into the aeration cell via tubing 102).

Referring to FIG. 4, an alternative to the use of the "syringe pump" 100 for providing repeated, controlled amounts of sample is shown. In this arragement, the solenoid valve 90 would be operated through control line 104 for a period of time during the system cycle enabling the sample to pass directly from the sample cylinder 80, through tubing 91 and valve 90 and tubing 94, into the aeration cell 52. During the processing of a previous sample, pump 74 (FIG. 2) would have filled and maintained sample cylinder 80 to the level of tube 84. Thus when the time comes to process the next sample, the hydrostatic pressure in cylinder 80 would be the same as the previous sample. This insures that the amount of sample supplied to the aeration cell 52 during the time in which solenoid valve 90 is open will be constant from sampling to sampling. Obviously with this sort of arrangement, the level of the fluid in cylinder 80 has to be higher than the point of entry, 107, in the cell 52.

The next aspect of the invention to be disucssed is the circulation system. Referring to FIG. 2, a sample of the air saturated, sample-containing liquid in the cell 52 is drawn off via duct 110. The latter is connected through a flow meter 111 to a peristaltic pump 112 such as the Masterflex$^{(R)}$ Tubing Pump, manufactured by The Barnant Corporation of Barrington, Illinois. The pump 112 forces the sample drawn off from the aeration cell 52 through a coil 114. The flow meter 111 provides an approximate measure of the volumetric pumping rate of pump 112, and is useful for adjusting the pump, 112, to the approximate flow rate desired.

The coil 114, typically might be on the order of 20 feet or more in length from end to end when stretched out. The coil, preferably, is manufactured from glass or suitable plastic. Prior to its use in this invention a sessile growth of microorganisms is formed within the coil. This is done by the continuous passage therethrough of a sludge-water suspension containing a suitably mixed biological culture. In time, in a manner similar to the deposition of slime by a running brook passing over rocks along its way, there is deposited on the sidewalls of the coil 114 a sessile film containing a mixed biological culture. This culture reacts with the oxygen and the organic material in the sewage or process effluent sample to cause the oxdiation reactions described in equations 1 and 2 above. This coil containing a biological culture might be termed a "biological reactor".

The pump 112 pushes the sample through the coil 114 and then through a piece of connecting tubing 116 to a flow coil 118. At this location there is positioned a dissolved oxygen (DO) probe 120, such as Model No, 39065, manufactured by the Beckman Company of Fullerton, California. The DO probe 120 is connected by wires 122 and 124 to a D.C. power source 126, such as model D-0.90-0.200-AI manufactured by the Dynage Company of Bloomfield, Connecticut, set at about 0.75 volts, and a signal detecting resistor 128 on the order of 10,000 ohms. Connected in parallel across the resistor 128 via wires 130 and 132 is a time recording device 134 such as Model 252 Chart Recorder with electronic integrator manufactured by Linear Instruments Corporation of Irvine, California. The recorder 134 plots a graphic representation of the oxidation reaction taking place in the sludge coil 114 by noting the oxygen level of the effluent sample after passing through the flow cell 118. The movement of the recording paper 136 in the recorder 134 will be as indicated by the arrow 138. Thus, as a point of reference the time $t_o$ in FIG. 1 appears at the right hand of the paper 136 as viewed in FIG. 2. The flow cell 118 is connected back to the aeration cell 52 through an additional length of tubing 140 via valve 141.

The valve 141 is useful in establishing an accurate measure of the volumetric pumping rate of pump 112. The accuracy of the Energy Oxygen measurement depends on this value as can be seen from equation 3, below. When calibrating the flow rate, valve 141 is turned such that the sample is made to exit from tube 143. A flask (not shown) of known volume, e.g. a twenty-five milliliter volumetric flask, is used to collect this liquid and a stop watch or other suitable timing device to measure the interval of time for the sample collection. In this manner a sufficiently accurate volumetric flow rate can be measured by dividing the 25.0 ml volume by the collection time.

In addition to the graph generated by the recorder 134, the electronic integrator contained therein can determine the area under the curve and provide an electrical signal which is a measure of the total oxygen consumed - the so-called Energy Oxygen. Certain constants such as the volumetric pumping rate of pump 112, the sample size (i.e. the volume of syringe 100a), a calibration constant for the DO probe 120 and a calibration constant for the recorder 134 could be supplied to the integrator, along with the electrical signal from the DO probe, in a fashion known to the profession. The integrator signal would then be a measure of energy oxygen when properly adjusted to utilize the following equation:

Energy Oxygen (ppm or mg of Oxygen/liter of sample) (3)
= Area × [Pump Rate (liters/min.)] × [ $\frac{1}{\text{Sample size (ml)}}$ ]
× [Probe Calibration (ppm dissolved oxygen/unit deflection)]
× Constant The integrator signal could be supplied to a printer which would provide a digital readout of energy oxygen along with other sample data such as time, sample number, etc. It may be desirous to correlate the energy oxygen data obtained with the biological oxygen demand (BOD) data mentioned earlier.

The correlation of energy oxygen and BOD values may be accomplished by using a standard BOD solution containing equal weight concentrations of glucose and glutamic acid as suggested in the BOD test procedure given in "Standard Methods for the Examination of Water and Wastewater," published by the American Public Health Association, 13th Edition. A variety of concentrations representing solutions with different BOD values can be tested by means of the herein described invention and by using the standard BOD test given in "Standard Methods". A correlation curve plotting energy oxygen against BOD values will show the numerical relationship of these two values for a series of concentrations of the standard BOD solutions.

In the event that solutions of pure substances such as sugar, amino acids etc. are to be analyzed by this herein described invention, a standard curve plotting known concentrations of these pure substances against the area of the energy oxygen diagram can be prepared thus enabling the determination of unknown concentrations of these pure substances in a manner known to the profession.

An alternate embodiment of the "biological reactor", coil 114 is a tube (it might measure for example, ½ inch in diameter and 6 inches in length) containing aggregate materials — pebbles or stones, fused glass, pieces of plastic, etc. — to achieve a very coarse filter upon which a sessile growth of microorganisms has been grown in a manner similar to that heretofore described.

Returning to FIG. 2, the fluid level in the aeration cell 52 is maintained at a constant level 142 by a decantation system which operates in conjunction with the previously described aeration system. The decantation system includes tubing 144 connected near the top of the aeration cell 52 at a level at which it is desired to decant the liquid 50. The tubing connects the aeration cell 52 to one port of solenoid valve 146 which is similar to those previously described. It responds to a voltage supplied on the control line 148 from timer 70. A second port is connected via tubing 150 to one end of a decantation jar 152 made of plastic or glass. The opposite end of the jar is connected via tubing 153 to an air bleed or ball valve 154. Simply, the ball valve 154 includes ports 155 and 156 for routing the air therethrough and port 158 which is opened or closed, in a manner soon to be described by, "ball" 159. Tubing 160 connects port 156 to a port on solenoid valve 66. The loop is closed through the aeration system previously described by means of tubing 65 which is connected to the vacuum port of the Neptune air/vacuum pump 64.

When the decant portion of the cycle is reached, voltages are supplied along control lines 69 and 148 to solenoid valves 66 and 146, respectively. As the pump 64 forces air into the aeration cell it draws a vacuum in line 65. During this time the solenoid valves connect tubing 65 to 160 and 150 to 144 respectively. The vacuum in the line "sucks" ball 159 into port 158 closing off the ball valve 154. The vacuum is thus transmitted through the valve 154 to the tubing 153. The vacuum draws off liquid above level 142 through the tubing 144, solenoid valve 146, tubing 150 and into the jar 152. The capacity of jar 152 is sufficient to handle the anticipated amount of decant liquid. The time for the decant portion of the cycle, likewise, is set to enable complete decantation. At the end of decantation, valves 66 and 146 are deenergized. This cuts off the vacuum to tubing 160, with port 68 again connected to tubing 65, and connects tubing 150 to port 162. The loss of vacuum in tubing 160 results in ball valve 154 "opening", allowing air to enter port 158. This releases the vacuum hold on the liquid in the decant jar 152. Thus the liquid drains therefrom through tubing 150, solenoid valve 146, and port 162 into the waste receptacle. The decant system is thus readied for the next sample.

OPERATION OF THE SYSTEM

Prior to operation of the system the DO probe 120 is calibrated to provide the probe calibration constant in equation 3. The calibration of the DO probe essentially consists of first bubbling the nitrogen through the fritted disc or aeration stone 54 and allowing the liquid in the total circulatory system to be purged completely of oxygen. The electrical signal (pen position on the recorder or maximum counts per minute at a digital readout for the integrator) will indicate zero ppm of DO and is one point for the calibration. Then air is passed through the disc or aeration stone 54 allowing the liquid in the circulatory system to be saturated with air. The temperature of the liquid is measured and the dissolved oxygen level is determined by referring to a *Solubility of Oxygen in Water* Table contained in "Standard Methods for the Examination of Water and Wastewater", published by the American Public Health Association. The electrical signal thus obtained represents the dissolved oxygen value at the solution temperature when the solution is saturated with air. The difference between the two signals can be used to obtain the calibration of the integrator and the recorder scale. A sometimes more convenient and obvious alternative to the above calibration procedure provides for passing first of all, water saturated, oxygen free gas, such as nitrogen, through the system to obtain the zero or no oxygen reading. After this, water saturated air whose temperature is known is passed through the system to obtain the air saturated or maximum calibration value for the DO probe. This value is obtained from the aforementioned table and is the same as for water at the given temperature, which is saturated with air.

To obtain the water-saturated gas in both instances, the respective gas is pumped through an aeration stone positioned in a container of water. The gas becomes laden with moisture, approaching a 100% humidity condition. After a period of time sufficient to insure the water-saturated condition, the gas is directed into the system and past the DO probe.

Whatever approach is utilized, these two readings are used to determine the probe calibration constant in the following manner: the "ppm dissolved oxygen" figure is obtained from the table mentioned above; from this is subtracted the probe reading when the oxygen free gas is pumped through. The deflection on the recorder is noted for both conditions and the "ppm dissolved oxygen/unit deflection" is obtained by dividing the "ppm dissolved oxygen" figure determined above by the difference in deflection readings.

As can be gathered from the description of the system above, the main control function for directing the various aspects of the system operation is the timer 70. This, typically, can be a multi-cam type where, through appropriate selection of cams, the routing of the main power voltage to the various solenoid valves previously mentioned can be effected in the necessary sequence. Note that throughout the cycle necessary for each sample certain portions of the system operate continuously. For example, the DO probe 120 and supporting power supply 126 and resistor 128, as well as the recorder 134, are operating continuously. Likewise the liquid 50 is continuously agitated by the bubbling air. The circulation system, including the pump 112, coil 114 and associated tubing, also processes the liquid 50 "endlessly".

It is important to note that the operating temperature of the liquids involved should typically be between 20° C and 35° C. Further, the operating temperature should be held relatively constant during a given test to insure a true and constant oxygen calibration value for the recorder and integrator scales.

The first event in the cycle is to start the external pump 74 through a control voltage on power line 78. The pump 74 supplies the cylinder 80 with a sample of sewage or process effluent. The sample level in the cylinder 80 rises until it reaches the level of the overflow duct 84. Concurrent with the operation of the pump 74, the decantation system is operated. This essentially requires energizing the two solenoid valves 66 and 146 via control lines 69 and 148 respectively. As described earlier, the pump 64 draws a vacuum in the tubing 65, 160, 153, and 150 through the solenoid valves 66, 146, and the ball valve 154, and the decant jar 152 such that any liquid in the aeration cell 52 in excess of the level 142 is drawn off via tubing 144. After the decantation system has been allowed to operate for a sufficient period of time, as noted earlier the two valves 66 and 146 are deenergized. The decant jar drains itself as described earlier.

While the sampling cylinder 80 is filling, solenoid valve 90 is energized so that tubing 91 is connected through the solenoid valve 90 to tubing 94. Likewise solenoid valve 92 is energized connecting tubing 94 to tubing 98 and blocking any connection to tubing 102. After the pump 74 has been on for a sufficient period of time to allow enough of the sample to collect in the sampling cylinder 80, in the one embodiment the syringe pump 100 would then be energized by the timer 70. The syringe 100a fills in response to the action of pump 100e. (In the embodiment of FIG. 4 the control voltage on line 104 would be delayed by the timer until the pump 74 could fill cylinder 80 to the level of overflow tube 84).

After the decantation of the system is completed and the solenoid valves 66 and 146 have returned to their rest positions, solenoid valves 90 and 92 are deenergized and switched to their rest positions (although not pictorialized in FIG. 2, it is obvious that the control voltage to solenoid valves 90 and 92 appearing on lines 104 and 106 can be provided by the same cam in timer 70 which provides the control voltages to solenoid valves 66 and 146). At this point the syringe pump, which, likewise can be controlled by the same cam as that which controls the solenoid valves 90, 92, 66 and 146, returns to its rest position which is the forward position of the syringe 100a, thereby injecting the sample liquid in the syringe into the aeration cell 52 through tubing 98, the solenoid valve 92 and tubing 102. After injection of the sample into the aeration cell 52, the cycle continues for a sufficient amount of time necessary to provide the oxidation reaction giving rise to the graph of FIG. 1 as pictorialized on the recording paper 136.

As noted earlier, the time necessary for the complete cycle including the steps of filling the sampling cylinder, decanting the aeration cell 52 and supplying a sample to the cell, is dictated by the biochemical oxidation process being carried on in the "biological reactor", coil 114. The cycle is assumed complete when the rate of oxygen consumption returns to the auto-oxidation line 30 of FIG. 1. Once the completed cycle is finished a new cycle can be initiated. The timer 70, aside from controlling the sequential processes noted above can also be manually advanced, in the event of a fast reaction to initiate a new cycle.

The sampling cylinder 80 is drained after every cycle since solenoid valve 90 is deenergized thereby connecting tubing 91 to port 96 which would discharge the sample 82 in cylinder 80 into the waste receptacle or drain.

Note that the various sections of tubing required to interconnect the elements of the system, typically, are made of non-toxic plastic material or metal such as stainless steel.

FIG. 5 discloses an alternate embodiment employing a sludge coil. The embodiment shown eliminates the possibility of any of the sludge contained in the coil and sloughed off or loosened by the flowing liquid from returning back to the aeration cell 52. This ensures that the reactions between the organic material and the microorganisms will take place completely in the coil.

In this embodiment, the peristaltic pump and the various pieces of equipment to be identified would correspond in manufacture to the devices referred to in the first embodiment of the invention.

The pump 200 is connected to a continuous supply of sewage or effluent in sample cylinder 202 via tubing 204. The sample is aerated in cylinder 202 as described above. Peristaltic pump 206 draws from a supply of air saturated water, contained in vessel 208 via tubing 210. Ordinary tap water supplied via tubing 212 would be aerated in vessel 208 in substantially the same way as described above. The pump 206 supplies the "pure", air saturated water, via tubing 214, to input port 216 of T-joint 218. The exit orifice 220, of the T-joint 218, is connected to flow meter 222. This in turn is connected to a coil containing the biological culture, 224, of the type described above.

The volumetric flow rate is measured by adjusting valve 221 to deliver sample through tubing 223 to a 25 milliliter volumetric flask (not shown). The time to fill the flask is measured accurately and the rate can be calculated as described above.

The peristaltic pump 200 is connected to the input port 225 of a solenoid valve 226 via tubing 228. The solenoid valve, under control of a timer 230 via control lines 231, either directs the air saturated sample supplied by pump 200 to a waste repository via outlet 232 or supplies it to input port 234 of the T-joint 218 via tubing 236.

Positioned at the exit end of the coil 224, is a DO measuring arrangement 238 similar to that described above. After passing through the measuring arrangement, the liquid is disposed of, into a waste repository or drain, via tubing 240.

OPERATION OF THIS EMBODIMENT

At the time when it is desired to make an energy oxygen measurement of the sample, the solenoid valve is energized by the timer. The solenoid then directs the air-saturated sample towards the T-joint connection for a specified period of time, consonant with the desired sample size. The pumping rates of pumps 200 and 206 are adjusted so that the water and sample are supplied to the T-joint such that they combine to form a mixture exiting therefrom which does not have an excessive concentration of pollutant for the amount of dissolved oxygen. The sludge in the coil 224 reacts with the organic material in the pollutant and the dissolved oxygen in the air saturated water. The sample then passes to the DO probe arrangement where the residual oxygen level is detected and the energy oxygen determined. The spent sample is then deposited in a waste receptacle.

A variation on this last described embodiment would allow for a determination of instantaneous changes in the concentration of organic material (pollutant concentration). Instead of pump 200 supplying sample for only a specified amount of time, it would supply sample continuously. This would provide a continuous monitor of the pollutant concentration.

The pumping rates of 200 and 206 are set so as to maintain a residual oxygen level (at the exit of the coil containing the biological culture) at all times, even when the rate of oxygen consumption is greatest, at or near the maximum of the energy oxygen curve 242 in FIG. 6. The DO arrangement 238 would first be calibrated so that the maximum portion of the curve 244 would correspond to the maximum concentration of pollutant for a given volume of air saturated liquid. As the sewage or effluent was pumped through the system, deviations from the maximum line would be proportional to changes in the pollutant concentration. Thus a continuous monitor of the concentration would be effected allowing for numerous applications obvious to those skilled in the art.

Those skilled in the art will recognize variations of the above described embodiments of the invention such as the following:

A. The determination of specific organic and inorganic substances or functional groups present in substances, which can be oxidized biologically by suitable bacterial species in the biological reactor.

The presence of inorganic substances (e.g. ammonia, nitrites, etc.) as well as organic substances for example amino, keto or aldehydo functional groups may be identified when suitable bacterial species are used in the biological reactor. For example, if it were desired to determine a particular sugar in a mixture of sugars, a species of bacteria which reacts with only that sugar would be used in the biological reactor. This species would biologically oxidize only the particular sugar of interest and the sugar could be determined by relating the energy oxygen to a standard.

B. The determination of the activity or potency of a bacteriocide, antibiotic or bacteriostat.

This might be achieved by contrasting the size and shape of the energy oxygen curve produced by a suitable bacterial species under standard conditions before and after a portion of that bacterial species were destroyed by a bacteriocide, antibiotic or bacteriostat. The potency of an unknown or new antibiotic could then by this method be related to the potency of a known antibiotic. Similarly a bacteriocide or bacteriostat would be determined in the same way.

Throughout the earlier discussion the type of material analyzed was always referred to as organic. This, however, is meant to imply not only organic substances but inorganic substances, such as ammonia, nitrites or other functional groups as well. The only basic criterion in this regard is that the substance or functional group be biologically oxidizable. Thus the word organic is to have the broader meaning just described and should not be limited to its traditional meaning either in the specification or appended claims.

As noted earlier, many other applications of the basic principles of this invention and the embodiments described herein will be apparent to those skilled in the art. The described embodiments are not to be construed as limitations on the scope of the invention. Rather, the invention is to be defined in its scope and breadth by the appended claims.

What is claimed is:

1. Apparatus for determining the amount of dissolved oxygen consumed by microorganisms while assimilating biologically oxidizable material in a liquid medium, comprising:
   a. first supply means for producing and supplying a liquid saturated with a gas containing oxygen;
   b. second supply means for introducing a measured sample of said liquid medium containing biologically oxidizable material into said oxygen containing liquid;
   c. reactor means containing said microorganisms in sessile condition and having an inlet and outlet port communicating with said first supply means, wherein said microorganisms consume a portion of said oxygen in reacting with said biologically oxidizable material;
   d. pump means interconnecting said first supply means and said reactor means for continuously recirculating said mixture of sample and oxygen containing liquid medium through said reactor means and said first supply means;
   e. analytical means for automatically measuring the amount of dissolved oxygen consumed by said microorganisms in said reactor means; and
   f. timer means interconnected with said second supply means, said pump means and said analytical means for causing the same to operate in a timed relation to one another.

2. The apparatus of claim 1 further comprising means for agitating said supply of oxygen containing liquid.

3. The apparatus of claim 1 wherein said first supply means includes:
   a. an aeration cell containing said oxygen containing liquid;
   b. third supply means for delivering oxygen or a gas containing oxygen into said aeration cell; and
   c. an aeration stone immersed in said liquid in said cell and interconnected with said third supply means.

4. The apparatus of claim 1 wherein the means of paragraph (e) comprises:
   a. means for measuring the concentration of dissolved oxygen in said recirculating mixture with time;
   b. means for measuring the volumetric rate at which said recirculating mixture is pumped through said vessel;
   c. means for integrating said concentration of dissolved oxygen with time; and
   d. means for combining the volumetric rate measurement and the output of said means for integrating and obtaining a result proportional to the total consumption of dissolved oxygen by said microorganisms.

5. The apparatus of claim 1 wherein said reactor means is a tube, a plurality of reaction sites containing bodies disposed within said tube, such reaction sites adapted to enhance the growth of said microorganisms thereon.

6. The apparatus of claim 1 wherein said reactor means containing said microorganisms is comprised of a coil about 20 feet long.

7. The apparatus of claim 1 including liquid level control means interconnected with said first supply means for removing any oxygen containing liquid therefrom which exceeds a predetermined level; said timer means also interconnected with said liquid level control means.

8. The apparatus of claim 1 wherein said second supply means includes means for providing a continuous supply of said liquid medium containing said biologically oxidizable material, said apparatus further comprising injection means for introducing successive amounts of said biologically oxidizable material containing liquid medium from said continuous supply means into said oxygen containing liquid in said first supply means.

9. The apparatus of claim 8 wherein said continuous means of supply includes storage means for storing a predetermined amount of said sample positioned over said first supply means, said storage means responsive to said injection means to deliver identical successive amounts of said sample thereto by gravity flow.

10. The apparatus of claim 8 wherein said means of control includes:
    a. a timer;
    b. a syringe pump; and
    c. a first and second valve, said first and second valve responsive to said timer to periodically connect said continuous means of supply to said syringe pump, said syringe pump responsive to said timer to thereby draw a predetermined amount of said sample, said second valve and said syringe pump further responsive to said timer and adapted to direct such drawn sample into said oxygen containing liquid at a prescribed point in the timer cycle.

11. The apparatus of claim 8 wherein said first valve is adapted, in responsve to said timer, to drain said continuous means of supply.

12. The apparatus of claim 8 further comprising means for decanting said supply of oxygen containing liquid when said liquid exceeds a predetermined level.

13. Apparatus for determining variations in the concentration of biologically oxidizable material in a liquid which comprises:
   a. means for producing and supplying oxygen containing liquid;
   b. means for supplying said liquid containing said biologically oxidizable material;
   c. means for mixing said supply of oxygen containing liquid with said liquid containing said biologically oxidizable material to form a mixture;
   d. a vessel of predetermined size containing a suitable microorganism growth situated therein having an inlet and an outlet;
   e. means for passing said mixture through said vessel from said inlet to said outlet; and
   f. calibrated means positioned at said outlet of said vessel for measuring the dissolved oxygen content of said mixture after it has passed through said vessel, said dissolved oxygen content being related to the amount of oxygen consumed by predetermined concentrations of said biologically oxidizable material.

14. A method for automatically determining the total consumption of dissolved oxygen in a liquid due to biologically oxidizable organic or inorganic material therein contained comprising the steps of:
   a. saturating a liquid with an oxygen containing gas;
   b. introducing a sample of liquid containing said organic or inorganic material into said oxygen containing liquid;
   c. circulating the liquid mixture resulting in step (b) at a fixed rate of flow through a reaction zone of predetermined length containing microorganisms; and
   d. measuring the level of dissolved oxygen in the mixture resulting in step (b) after it passes through said reaction zone.

15. The method of claim 14 further including the step of returning the level of said oxygen containing liquid to a predetermined level after step (d).

16. The method of claim 14 wherein step (d) includes the steps of measuring the rate of oxygen consumption with time and integrating said rate of oxygen for the time of said measurement to obtain the total consumption of dissolved oxygen due to said biologically oxidizable material.

17. The method of claim 14 wherein said biologically oxidizable material includes a specific substance and said biological growth is a species of microorganisms which can biologically oxidize said specific substance.

18. A method for automatically determining the bacteriocidal potency of a bacteriocide of unknown potency comprising the steps of:
   a. measuring the energy oxygen of a measured amount of a first standard biologically oxidizable material of scientifically established or known potency by carrying out the steps of claim 14;
   b. measuring the energy oxygen of a like measured amount of a second biologically oxidizable material of scientifically unknown potency out the steps of claim 36;
   c. comparing the energy oxygen of step (a) and (b) to determine the potency of said second material.

* * * * *